United States Patent
Bastide et al.

(10) Patent No.: US 12,014,836 B2
(45) Date of Patent: Jun. 18, 2024

(54) STREAM INTEGRITY FOR ARTIFICIAL INTELLIGENCE CONVERSATIONS

(71) Applicant: International Business Machines Corporation, Armonk, NY (US)

(72) Inventors: Paul R. Bastide, Ashland, MA (US); Matthew E. Broomhall, Goffstown, NH (US); Robert E. Loredo, North Miami Beach, FL (US)

(73) Assignee: International Business Machines Corporation, Armonk, NY (US)

( * ) Notice: Subject to any disclaimer, the term of this patent is extended or adjusted under 35 U.S.C. 154(b) by 477 days.

(21) Appl. No.: 17/117,461

(22) Filed: Dec. 10, 2020

(65) Prior Publication Data

US 2022/0189643 A1    Jun. 16, 2022

(51) Int. Cl.
| | |
|---|---|
| *G10L 15/28* | (2013.01) |
| *G06F 18/24* | (2023.01) |
| *G06N 5/04* | (2023.01) |
| *G16H 80/00* | (2018.01) |

(52) U.S. Cl.
CPC ............. *G16H 80/00* (2018.01); *G06F 18/24* (2023.01); *G06N 5/04* (2013.01)

(58) Field of Classification Search
CPC ................................ G16H 80/00; G10L 15/28
See application file for complete search history.

(56) References Cited

U.S. PATENT DOCUMENTS

| | | |
|---|---|---|
| 9,633,674 B2 | 4/2017 | Sinha |
| 9,805,718 B2 | 10/2017 | Ayan et al. |
| 10,175,865 B2 | 1/2019 | Beaver et al. |

(Continued)

FOREIGN PATENT DOCUMENTS

WO    WO-2021071971 A1 *    4/2021

OTHER PUBLICATIONS

Tian, Shuo, et al. "Smart healthcare: making medical care more intelligent." Global Health Journal 3.3 (2019): 62-65. (Year: 2019).*
"User," Facebook for Developers, Printed Dec. 7, 2020, 27 pages https://developers.facebook.com/docs/graph-api/reference/user.
"Graph API Reference /{user-id}/friends," Facebook for Developers, Printed Dec. 7, 2020, 7 pages https://developers.facebook.com/docs/graph-api/reference/user/friends.

(Continued)

*Primary Examiner* — Jason B Dunham
*Assistant Examiner* — Constantine Siozopoulos
(74) *Attorney, Agent, or Firm* — Jared C. Chaney

(57) ABSTRACT

A method, system, and computer program product to prevent misinterpretation of communications via artificial intelligence assistants. The method includes monitoring an artificial intelligence enabled communication. The method also includes analyzing messages, participants, and actions within the communication. The method also includes identifying critical data within the communication. The method also includes determining critical sequence data, where the critical sequence data is a sequence of conversation elements that contains the critical data. The method also includes predicting an uncertainty level for the critical sequence data, where the uncertainty level indicates an amount of uncertainty that the artificial intelligence correctly interprets the critical sequence data. The method also includes determining that the uncertainty level for the critical sequence data is above a threshold uncertainty value, resulting in critical sequence data that is subject to misinterpretation. The method also includes resolving any uncertainties for the critical sequence data.

20 Claims, 5 Drawing Sheets

(56) References Cited

U.S. PATENT DOCUMENTS

| | | | |
|---|---|---|---|
| 2018/0374475 A1 | 12/2018 | Lewis et al. | |
| 2020/0117858 A1* | 4/2020 | Freeman | G06F 40/35 |
| 2020/0243186 A1* | 7/2020 | Gallopyn | G16H 40/20 |

OTHER PUBLICATIONS

Dinan et al., "Advances in Conversational AI," Facebook AI, Aug. 2, 2019, 7 pages https://ai.facebook.com/blog/advances-in-conversational-ai/.

Welleck et al., "Dialogue Natural Language Inference," Cornell University, arXiv:1811.00671v2 [cs.CL] Jan. 18, 2019, 11 pages, https://arxiv.org/abs/1811.00671.

"Babylon: 24/7 Appointments," Babylon Health, Printed Dec. 7, 2020, 4 pages https://itunes.apple.com/in/app/babylon-health/id858558101?mt=8.

"Texting + Video with No App Required. The Patient Experience—Reimagined.," OhMD, Printed Dec. 7, 2020, 12 pages, https://www.ohmd.com/patient-communication/.

"Gnip APIs," GNIP, Printed Dec. 7, 2020, 4 pages, http://support.gnip.com/apis/.

"Natural Language Classifier," IBM, Watson, Printed Dec. 7, 2020, 10 pages https://www.ibm.com/watson/services/natural-language-classifier/.

Pham et al., "A Situation-Based Multi-Agent Architecture for Handling Misunderstandings in Interactions," International Journal of Applied Mathematics and Computer Science, University of Zielona Gora, vol. 25, No. 3, 2015, pp. 439-454, DOI: 10.1515/amcs-2015-0033.

Pham et al., "Handling the Misunderstanding in Interactions: Definition and Solution," ResearchGate, International Conference on Software Engineering & Applications, Singapore, Dec. 2011, pp. 47-52.

Fadhil et al., "Designing for Health Chatbots," Printed Nov. 5, 2020, 20 pages, arXiv:1902.09022.

"Push technology," Wikipedia the Free Encyclopedia, Printed Dec. 7, 2020, 7 pages https://en.wikipedia.org/wiki/Push_technology.

"Webhook," Messenger Platform, Facebook for Developers, Printed Dec. 7, 2020, 7 pages https://developers.facebook.com/docs/messenger-platform/webhook.

\* cited by examiner

STREAM INTEGRITY FOR ARTIFICIAL INTELLIGENCE CONVERSATIONS

BACKGROUND

The present disclosure relates to artificial intelligence and, more specifically, to preventing misinterpretation of communications via artificial intelligence assistants.

Conversational platforms are used to connect people and information in logical and organized ways in order to accomplish a task or purpose. With the increase in technology, conversational platforms are becoming more and more frequent in various uses such as healthcare, customer service, information technology (IT) assistance, etc. Further, conversation platforms are often used for conversations between a person (for example, a user) and a computer system, such as an artificial intelligence (AI) computer system (or a computer system connected to AI technology). AI technology and/or computer systems display and execute cognitive functions that have previously been associated with humans. For instance, AI allows computers to learn, reason, problem solve, etc. AI may also be capable of interpreting natural language speech and writing. Therefore, AI enabled conversational platforms (for example, conversations with an AI assistant) may be used to support communication between a user and AI technology (such as an AI assistant).

SUMMARY

The present invention provides a computer-implemented method, system, and computer program product to prevent misinterpretation of communications via artificial intelligence assistants. The method includes monitoring an artificial intelligence enabled communication. The method also includes analyzing messages, participants, and actions within the communication. The method also includes identifying critical data within the communication, where the critical data is data that is important for performing the actions within the communication. The method also includes determining critical sequence data, where the critical sequence data is a sequence of conversation elements that is within the communication and that contains the critical data. The method also includes predicting an uncertainty level for the critical sequence data, where the uncertainty level indicates an amount of uncertainty that the artificial intelligence correctly interprets the critical sequence data. The method also includes determining that the uncertainty level for the critical sequence data is above a threshold uncertainty value, resulting in critical sequence data that is subject to misinterpretation. The method also includes, in response to determining that the critical sequence data is subject to misinterpretation, resolving any uncertainties for the critical sequence data. The system and computer program product may include similar steps.

The above summary is not intended to describe each illustrated embodiment or every implementation of the present disclosure.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

Figure 1:
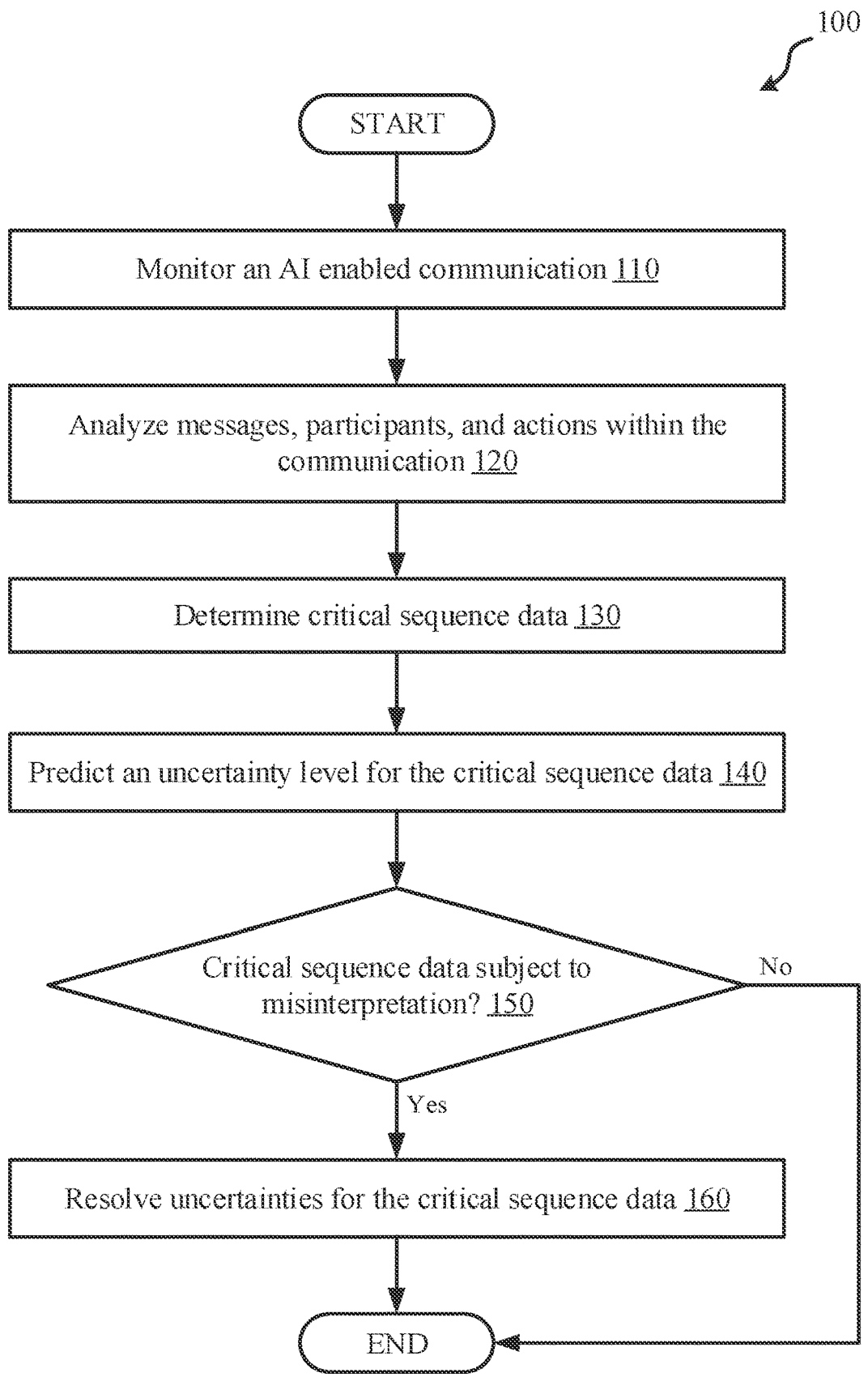
FIG. 1 depicts a flowchart of a set of operations for preventing and resolving any uncertainties in artificial intelligence enabled communications, according to some embodiments.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

Aspects of the present disclosure relates to artificial intelligence and, more specifically, to preventing misinterpretation of communications via artificial intelligence assistants. While the present disclosure is not necessarily limited to such applications, various aspects of the disclosure may be appreciated through a discussion of various examples using this context.

As discussed herein, artificial intelligence (AI) technology is increasingly used in conversational platforms for communication with a user. For example, when a user needs IT assistance, a user may go through a chat service and may chat with an AI assistant (for example, an AI chat bot) to try and resolve the issue. In some instances, the AI assistant may be assisting a human who may be working to resolve the issue for a user. For example, a user, an AI assistant, and an agent may all be participants in a chat service and the human agent and the AI assistant may be working together to resolve the user's issue. However, although AI has become increasingly effective, AI is not always accurate in interpreting natural language. For instance, many conversational platforms may base their analysis of the conversation on asynchronous technologies or communications, and may interpret user responses as responding to the most recent message from the AI assistant. Therefore, conventional conversational platforms may be unstable, inconsistent, and/or not accurate in their interpretation and execution of conversing with a user.

In certain industries, such as the healthcare industry, an inaccuracy in interpreting a chat from a user may result in misdiagnoses and/or improper treatment for a user, which could be very harmful to the user. For instance, if an AI assistant includes multiple questions in a message, or asks multiple questions before a user responds, the AI assistant may be at risk of misinterpreting the response. For example, an AI assistant may send a message to a user stating, "I am going to ask you a few questions to help diagnose what might be causing your headache" and then may follow up with a second message stating, "How was your head pain this morning?" In this example, the user may respond to the AI assistant with the message "alright" immediately following the second message. However, the user may have intended the "alright" message to be in response to the message "I am going to ask you a few questions to help diagnose what might be causing your headache" but the AI assistant may interpret the message as a response to the message "How was your head pain this morning?," due to the proximity to the second message. In this example, the user's headache may get misdiagnosed as a short-term headache, because the AI assistant may have interpreted that the user did not have head pain that morning, instead of correctly diagnosing the user with a long-lasting headache, as the user may have had a headache for over 24 hours.

The present disclosure provides a computer-implemented method, system, and computer program product for preventing misinterpretation of communications via artificial intelligence (AI) assistants. In some instances, the communications may be through push message, pull feed, user interface, etc. To prevent misinterpretation and therefore increase the accuracy of conversational platforms with AI assistance, conversations between a user and an AI assistant may be monitored and analyzed in order to determine whether there is any data and/or any sequences of data where it is critical, or at least important, for the purposes of the communications. For example, if the communications relate to healthcare, then any communications about the issue (such as whether the user is in pain, where the pain is located, etc.) may be critical to the purpose of diagnosing/giving advice to the user. In another example, if the communications relate to finance, then any communications about the financial issue (such as the user's income, whether the user is in dept, etc.) may be critical for the purposes of the financial communication.

For the portions of the communication that include critical data, it may be predicted how unstable the critical data is, or how likely it is that the AI assistant may misinterpret the critical data. If the critical data is at risk of being misinterpreted, then the conversation may be stabilized (for example, by following up with clarifying questions, pausing the conversation to wait for an answer to a critical question, placing injection markers into the conversation to clarify which messages correspond, and/or (if necessary) introducing a human agent to the conversation to re-stabilize the conversation and resolve any issues).

Referring now to FIG. 1, a flowchart illustrating a method 100 for preventing and resolving any uncertainties in artificial intelligence enabled communications is depicted, according to some embodiments. In some embodiments, method 100 is executed by a server (e.g., computer system/ server 502 (FIG. 5)) on or connected to a computer system (e.g., computer system 500 (FIG. 5)). In some embodiments, the method 100 is implemented as a computer script or computer program (e.g., computer executable code) to be executed on or connected to the computer system. In some embodiments, method 100 is executed on an artificial intelligence system (e.g., artificial intelligence system 422 (FIG. 4)). In some embodiments, method 100 is executed on a provider system (e.g., provider system 424 (FIG. 4)) connected to an artificial intelligence system.

Method 100 includes operation 110 to monitor an artificial intelligence (AI) enabled communication. An artificial intelligence enabled communication is a communication between a user and AI intelligence (for example, an AI assistant and/or bot). In some instances, the AI enabled communication is through a conversational platform. For example, a user may send a message (through a user computer system) to a healthcare AI assistant through a conversational platform in order to help diagnose a health issue with the user. AI enabled communication (for example, through conversational platforms) is becoming more frequent and may help more efficiently assist the user (compared to the user either having to schedule an appointment or wait in a phone queue to talk to a human assistant), while also helping prevent overloading on provider systems (because the assistance may be more evenly disbursed between phone queues, AI chat assistance, in person appointments, etc.). Communications, as referred to herein, may refer to the conversations between the user system and the provider system (for example, via conversational platforms enabled with AI). Monitoring the AI enabled conversation may include observing the components of the communication (for example, between the user computer system and an AI assistant).

Method 100 includes operation 120 to analyze messages, participants, and actions within the communication. In some embodiments, the user has to grant permission for access to user information (for example, before utilizing the AI enabled communication). In some embodiments, a user may have an already standing agreement (for example, an agreement to release information, a confidentiality agreement, etc.) with the provider (the party providing the assistive services). Once a communication is started and monitored, the computer system (for example, a provider system) may analyze various aspects of the communication. Some of those various aspects may include messages, participants, and actions. Messages may refer to the individual messages that make up the communication. For example, a first message may be sent from a user to an AI assistant. A second message may then be sent, in response to the first message, from the AI assistant to the user. The collective messages exchanged between the user and the AI assistant, in this example, may make up the communication between the user and the AI assistant.

Participants may refer to the various parties that have access to the communication. In some instances, the participants of the communication may simply be the user and the AI assistant (and, in some instances, the provider party who owns and/or has access to the AI assistant). In some instances, providers (for example, individuals who help provide the assistive services to the user) through the provider party may also have access to the communication. For example, providers may be available to provide assistance if the AI assistant is unable to, and those providers may have access to the communication in order to provide assistance, if necessary. In some instances, when analyzing participants of the communication, the system may only analyze the parties that have participated in the conversation. In some instances, when analyzing participants of the communication, the system may analyze all parties who may be able to access the communication.

Actions may refer to the purposes of each message (or components within the message) of the communication. For instance, an message from the user indicating "I have a fever" may be a diagnosis action and/or an action identifying the problem. Further messages from the AI assistant such as "do you have any other symptoms?" may be a further diagnostic action to help clarify the problem. In some instances, particularly in healthcare situations, the actions may include diagnosis actions, treatment actions, and gather information actions. Messages that gather information may include messages gathering initial information that will help provide a diagnosis of the problem, gathering information (for example, after the diagnosis) that will help the AI assistant determine a treatment for the diagnosis, etc. Messages that relate to the diagnosis may include messages that help identify the problem that the user has. Messages that relate to the treatment may include messages providing treatment information on how to resolve the problem.

In some embodiments, data from the communication may be loaded into an analytic data store after it is received. In some instances, it is loaded into the analytical data store using the following schema:

Message Details {Body, Subject, Metadata}
Topic Concepts/Category [Concept-1, Concept-2, Concept-3, . . . ]
Unique Message Identifier
Conversation Identifier
Access Control
Owner
Location
Tenant
Terminal The message details may break down the specific components of the message. For example, a message stating "My head hurts" may be organized into a format such as {hurt head, head, injury}. The hurt head may be the information provided in the body of the message, head may be the subject of the message, and the message may have metadata for (or may provide more information for) an injury of the user. The various elements (for example, messages) of the communication may correspond to various concepts or categories within the communication. For example, in a healthcare situation, one concept could be diagnosis and another concept could be treatment. In this example, the topic concepts schema may indicate whether the message relates to diagnosis or treatment. In another example, the various elements of the communication may organized (or categorized) based on the ailment. For example, in the same communication, a user may mention an injured head, a broken toe, and a sore throat. In this example, the topic schema may indicate whether each message and information within the messages relate to the injured head, the broken toe, or the sore throat.

In some embodiments, the unique message identifier is a message ID for the specific message. Each message may have their own unique message ID. In some instances, the unique message identifier is generated or extracted from the message. The conversation identifier (from the data store schema) may be a unique conversation ID for the communication as a whole. In some instances, the conversation identifier is generated or extracted from the communication. Access control (from the data store schema) may be a membership list for the communication indicating who has access to the communication. The owner may be the owner or author of a message from the communication. Different messages within the communication may have different owners, as they may be authored by different users and/or the user and the AI assistant. The location may indicate the approximate location the message was sent from. In some instances, the location information may not be known for various messages, depending on user settings and/or provider settings. The tenant may be the assigned company, client, group, etc. for sharing the data and storing the data in a data store. For example, if a user is messaging an AI assistant about healthcare questions, the healthcare provider may be the assigned company who has access to the user data, stores the user data, etc. Terminal, from the data store schema, indicates whether the message was the end of the communication. Each message from the communication may not include every element of the data store schema. For example, if a message is not the last message of the communication, then the message is not the terminal message. In instances when the communication is loaded (for example, by the provider) into a data store, the various schema used may be used to help analyze the messages, participants, and actions of the communication.

Method 100 includes operation 130 to determine critical sequence data. This may be based on the analyzing (operation 120). In some embodiments, critical sequence data is a sequence of conversation elements within the communication that contain critical data. Conversation elements are individual elements (for example, messages) within the communication. Critical data may be data within the conversation elements that is critical, or very important, in performing the various actions. For example, a message within the communication stating, "I was walking in my house and stubbed my left toe on a bookshelf" includes critical data such as "stubbed my left toe," as this data is critical in diagnosing the problem (likely an injured toe). The other information in the message is likely not critical data as it is not helpful in diagnosing, treating, or gathering information (to diagnose or treat the problem). In some embodiments, there may be critical data that is not in a sequence. For example, a first message from a user may state "my head hurts" and then another message from the user much later on in the communication may state "I also have arm pain." These messages may both include critical data, however they correspond to unrelated issues and are not in sequence with each other, therefore the two messages may not include critical sequence data.

In some instances, critical sequence data may already exist within the communication. For example, the AI assistant may have transmitted a message stating, "Where did you hit your head?" and the user computer system may have replied with a message stating, "On the front left portion of my forehead." The combination of the two messages (or components within the messages) may be the critical sequence data. In some instances, the critical sequence data may not fully exist within the communication. For instance, the critical sequence data may include one already existing element (in the communication) to the sequence and one element that is predicted to be added to the communication. For example, the AI assistant may have transmitted the message stating, "Where did you hit your head?" however the user computer system may not have transmitted the reply message yet. In this example, because the AI assistant asked a question, it may be predicted that the user computer system will transmit a reply, and therefore the critical sequence data may be the existing message as well as the predicted reply message (predicted to contain critical data to help with the diagnosis). Determining critical sequence data is discussed herein and depicted in FIG. 2.

Method 100 includes operation 140 to predict an uncertainty level for the critical sequence data. In some embodiments, the uncertainty level indicates an amount of uncertainty of the AI (e.g., an AI assistant and/or bot) correctly interpreting the critical sequence data. For example, if the critical sequence data includes data from a sequence of two messages, one in reply to the other, the first stating, "What is your yearly salary?" and the second stating, "My salary is $50,000," then the uncertainty level for interpreting the critical sequence data is pretty low. In another example, there are three messages, the first from the AI assistant stating, "What is your yearly salary?," then a second message from the AI assistant stating, "How much is remaining on your mortgage for your house?," and then a message from the user stating, "$50,000." In this example, there may be a large uncertainty level for the critical sequence data (including critical data from the sequence of three messages) because it is unclear whether the $50,000 is what is remaining in the mortgage or whether it is the user's yearly salary.

A large uncertainty level for the critical sequence data may indicate that the AI assistant has a large chance of wrongly interpreting the critical data. Wrongly interpreting the critical data could have a significant impact on AI assistant's solution to the problem (for example, treatment plan, finance advice, etc.) which may result in unintended consequences for the user. Predicting the uncertainty level for the critical sequence data is further discussed herein in relation to FIG. 3.

Method 100 includes operation 150 to determine whether the critical sequence data is subject to misinterpretation based on the uncertainty level. In some instances, if the uncertainty level is high (for example, above a threshold uncertainty value), then the critical sequence data is subject to misinterpretation. The threshold uncertainty value may be set by the AI technology system (or owners of the AI system) and/or the provider system (or owners of the provider system). If it is uncertain whether the AI assistant will interpret the critical sequence data correctly, then the AI assistant may be likely to misinterpret the critical sequence data, which may result in consequences for the user. For example, continuing the example above, with it being uncertain whether the $50,000 is the annual salary of the user or the remaining amount to pay on the user's mortgage, the user may have a large yearly salary (such as $200,000), may not have many monthly expenses, and may have $50,000 remaining on their mortgage. In this example, the correct solution for the user may be to pay off their remaining mortgage as soon as possible (because they have the available resources to do so). However, in this example, if the AI assistant interprets the $50,000 as the yearly salary, the AI assistant may instruct the user to refinance their mortgage and pay it off over a longer period of time, which would be incorrect advise for the user in their situation. Determining whether the critical sequence data is subject to misinterpretation is further discussed herein in relation to FIG. 3.

If it is determined, in operation 150, that the critical sequence data is not subject to misinterpretation, then method 100 ends after operation 150. If the critical sequence data is not subject to misinterpretation, then it is not likely that the AI assistant will incorrectly interpret critical data from the user, and there is less risk that the AI assistant will offer poor advise, suggest incorrect actions, etc. for the user. Therefore, if the critical sequence data is not subject to misinterpretation, the AI assistant may proceed using conventional methods to resolve the inquiries, issues, etc. from the user.

If it is determined, in operation 150, that the critical sequence data is subject to misinterpretation, then method 100 proceeds to operation 160 to resolve uncertainties for the critical sequence data. If the critical sequence data is subject to misinterpretation, then the AI assistant may be likely to misinterpret the critical data, which may result in unintended consequences for the user. For example, in healthcare situations, the user may end up being misdiagnosed and may be suggested treatments that may not help solve the actual issue, and may even harm the user in certain circumstances. Therefore, if the critical sequence data may be misinterpreted, then any uncertainties with the critical sequence data should be resolved before the AI assistant proceeds (for example, with treatment suggestions).

In some instances, particularly when a message (or conversation element) containing critical sequence data has not been received yet, resolving the uncertainties for the critical sequence data may include stopping progress in any conversation elements relating to the critical sequence data until the conversation element is received. For example, an AI assistant may send a message asking, "When did you start having pains?" In this example, it is predicted that a conversation element (e.g., message) will be received from the user answering the question from the AI assistant. Instead of asking follow up questions or adding any conversation elements that could lead to misinterpretation, the system may pause any messages from the AI assistant, or at least messages relating to the critical sequence data (for example, data about the pains) until a response to the inquiry is received from the user. This may stop progress in conversation elements relating to the critical sequence data, thus preventing misinterpretation from the AI assistant.

In some instances, resolving any uncertainties for the critical sequence data may include identifying which conversation elements (for example, messages) within the communication contain the critical sequence data (referred to herein as critical conversation elements) and then labelling the critical conversation elements as unresolved. For example, using the previous example with the three conversation elements containing critical sequence data, "What is your yearly salary?," "How much is remaining on your mortgage for your house?," and "$50,000," all three messages may be determined to be critical conversation elements. In this example, once these messages are identified as critical conversation elements, they may be labelled (for example, flagged, marked, etc.) as unresolved. In some instances, the labels are visible to the AI system and the AI system may know that it needs to resolve the labelled unresolved issues before proceeding. In some instances, the labels may also be available to the user conversing with the AI assistant, and the user may be able to send in follow up messages clarifying the unresolved issues. In some embodiments, the user may be able to mark or select the order in which the critical conversation elements should be interpreted in order to resolve the uncertainties.

In some instances, resolving any uncertainties for the critical sequence data includes transmitting clarifying inquiries to the user. The clarifying inquiries may be used to clarify the conversation elements that relate to the critical sequence data. For example, continuing the above example with critical conversation elements stating, "What is your yearly salary?," "How much is remaining on your mortgage for your house?," and "$50,000," the AI assistant may reply with a clarifying inquiry "Is there $50,000 remaining on your mortgage?" If the user responds "Yes," then the AI assistant may respond with a second clarifying inquiry stating, "What is your yearly salary?" If the user responds "No," the AI assistant may respond with a second clarifying inquiry stating, "Is your yearly salary $50,000?" In some instances, the AI assistant may continue to transmit clarifying inquiries until all uncertainties and/or issues relating to the critical sequence data are resolved, and the AI assistant is not at risk of misinterpreting critical data.

In some embodiments, the provider system (or an owner of the provider system) may determine how to resolve the uncertainties for the critical sequence data. For instance, the provider system may have resolution actions that they prefer over others and the provider system may include an order and/or circumstances in which to apply the various resolution actions. In some embodiments, the AI system (or an owner of the AI system and/or AI technology) may determine how to resolve (for example, which resolution actions to apply and when) the uncertainties.

Figure 2:
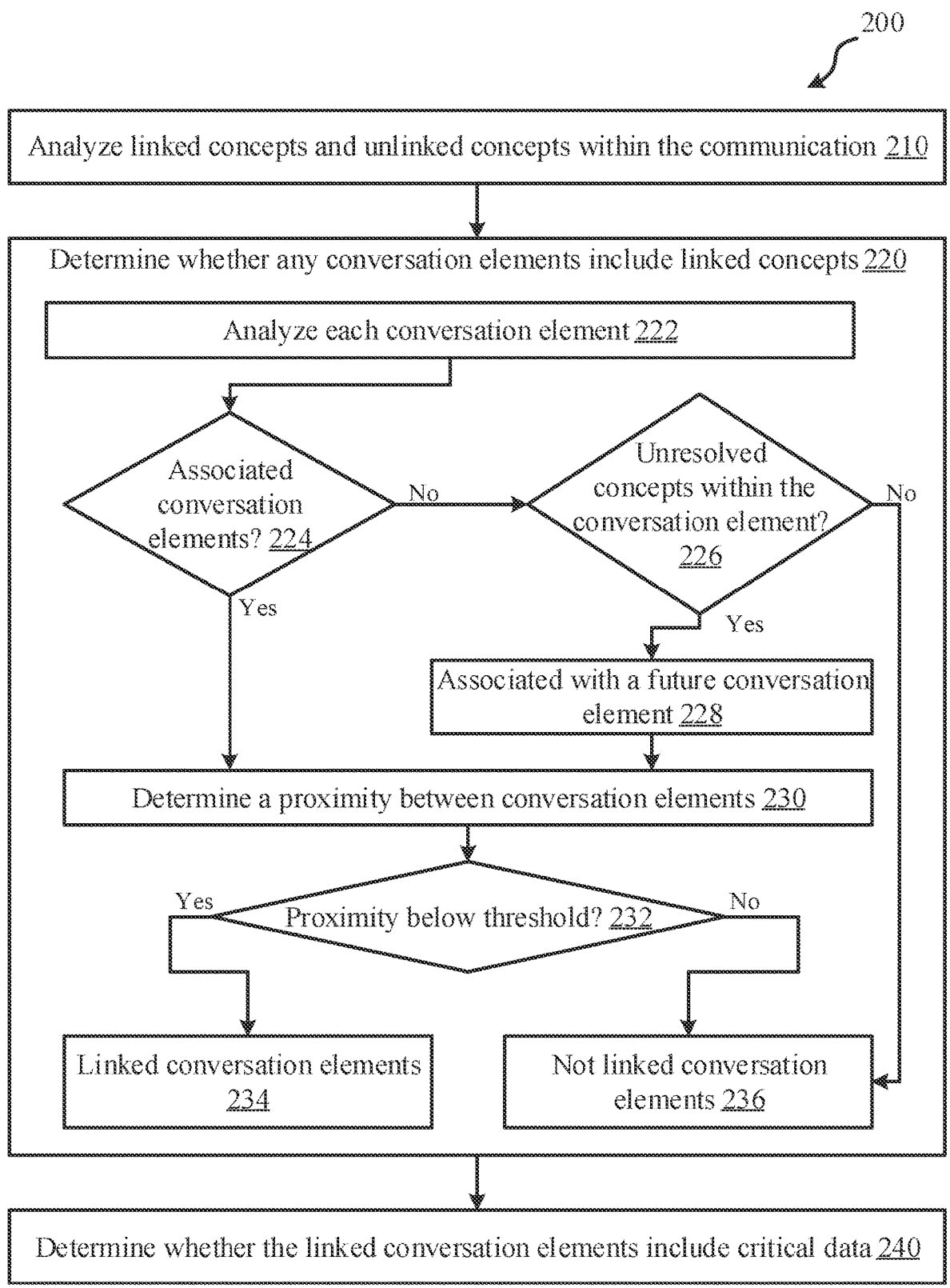
FIG. 2 depicts a flowchart of a set of operations for determining critical sequence data, according to some embodiments.

Referring to FIG. 2, a flowchart illustrating a method 200 for determining critical sequence data is depicted, according to some embodiments. In some embodiments, method 200 corresponds to operation 130 of FIG. 1. Method 200 includes operation 210 to analyze linked concepts and unlinked concepts within the communication. Linked concepts may be concepts or components within the communication that are related to each other. Unlinked concepts may be concepts or components within the communication that are not related (or not significantly related) to each other. In some instances, which each conversation element is received (for example, by the AI assistant), the system (for example, the provider system, with the AI assistant on or connected to the provider system) calculates the concept complexity for the concepts within the conversation element and the interdependency of the concepts within the conversation element to prior conversation elements within the communication. For example, a message "my head hurts" may not have a very high concept complexity compared to a message "I had a concussion a year ago, I slipped and fell this morning, and now the back of my head is throbbing." However, in this example, both messages could be determined to have concepts relating to a head injury, and therefore could be determined to be linked. Further, in some instances, the concept complexity of each statement may help affirm that the two concepts are linked. In human conversations, there is commonly a pattern to start broadly and then build on the broad concepts with more information. Determining concept complexity may help identify instances where a user is building upon a concept they have already introduced, therefore helping show that concepts within the messages are linked.

Method 200 includes operation 220 to determine whether any conversation elements include linked concepts. Once the various linked and unlinked concepts within the communication are analyzed, it may be determined where the various linked concepts are located. For example, if one individual message contains linked concepts, but the concepts are not located in any other messages, then only the one conversation element includes the linked concept. However, in other instances, two different conversation elements (e.g., messages) may include the linked concept.

Determining whether any conversation elements include linked concepts includes operation 222 to analyze each conversation element within the communication. Analyzing the conversation elements may include identifying the subject, components, etc. of each conversation element within the communication.

Determining whether any conversation elements include linked concepts also includes operation 224 to determine whether there are any associated conversation elements. In some embodiments, associated conversation elements may be conversation elements within the communication that contain the same linked concept. For example, a first conversation element from an AI assistant may ask, "Where have you been injured?" and a second conversation element from a user may state "On my foot." In this example, the second conversation element immediately follows the first conversation element, and both conversation elements discuss the same concept of injury and diagnosing the issue. Therefore, in this example, the first and second conversation elements are associated conversation elements. In some embodiments, associated conversation elements may be conversation elements that contain the same linked concept, but are not next to each other within the communication. For example, there may be some instances where multiple concepts are being discussed simultaneously. In this example, there may be a first message from an AI assistant asking, "Where have you been injured?" and a second message asking, "Has your sore throat been treated?" (for example, in response to a previous communication between the AI assistant and the user). In this example, the user may respond stating, "On my foot" and a second message stating, "Yes." In this example, "Where have you been injured?" and "On my foot" may be associated conversation elements, and "Has your sore throat been treated?" and "Yes" may be associated conversation elements.

If there are any associated conversation elements, in operation 224, method 200 proceeds to operation 230 to determine a proximity between conversation elements. In some instances, the associated conversation elements that are within close proximity to each other (for example, with not many, or any, messages in between) it may be more difficult to correctly interpret each conversation element, particularly when there are multiple questions within the various messages. For example, if there are multiple messages being exchanged about head pain, location of head pain, level of head pain, how hard the user hit their head, etc. a user responding with a message "strong" could reasonably be interpreted as a response to the level of head pain and how hard the user hit their head. Operation 230 is discussed further herein.

If there are not any associated conversation elements, in operation 224, method 200 proceeds to operation 226 to determine whether there are unresolved concepts within the conversation element. As discussed herein, there may be instances where there is a conversation element that is predicted to be associated with an existing conversation element, however the conversation element may not have been received by the AI assistant and/or the providing computer system yet, and therefore may not be considered an associated conversation element (for example, as discussed in operation 224). For example, an AI assistant may have asked a question but may not have received an answer for the question yet. An unresolved concept may be a concept (for example, diagnosing the injury) that has not been resolved yet. A question "How much pain are you in?" without an answer may be an unresolved concept, in some instances. In some instances, unresolved concepts may have a strong likelihood of prompting future messages or conversation elements.

If there are not any unresolved concepts within the conversation element, in operation 226, method 200 proceeds to operation 236 to determine that the conversation element is not linked to any other conversation elements. In these instances, the conversation element is not associated with any existing conversation elements nor is the conversation element predicted to be associated with a future conversation element (because the conversation element does not include any unresolved concepts), therefore it is determined that the conversation element is not a linked conversation element.

If there are any unresolved concepts within the conversation element, in operation 226, then method 200 proceeds to operation 228 to determine that the conversation element is associated with a future conversation element. As discussed herein, if the conversation element includes unresolved concepts (for example, by including a question in the conversation element), then it may reasonably be predicted that a future conversation element will be received that is associated with the existing conversation element. In those instances, even though the future conversation element has not been received yet, the existing conversation element and the future conversation element may be treated as associated conversation elements and the method may proceed to operation 230.

In operation 230 a proximity between conversation elements is determined. In some instances, the proximity between elements may be a number of elements between the two associated conversation elements. For example, "Where on your foot have you been injured?," "Has your sore throat been treated?," "My heel," and "Yes," may include two pairs of associated conversation elements—"Where on your foot have you been injured?" and "My heel," and "Has your sore throat been treated?" and "Yes." In this example, each pair of associated conversation elements may have a proximity of one, as there is one conversation element between each associated conversation element. In another example, using the previous example with the messages "What is your yearly salary?," "How much is remaining on your mortgage for your house?," and "$50,000," all three messages may be associated messages with a proximity of zero, or in some instances, one, between each message, as they are right next to each other.

In some instances, the proximity may also consider the day/time between associated conversation elements. For instance, using the above example, if "What is your yearly salary?" was sent at 12:02 PM, "How much is remaining on your mortgage for your house?" was sent at 12:04 PM, and "$50,000" was sent at 12:05 PM, then it is likely that the $50,000 could be in response to either question, as they were all sent around the same time. In this example, the message "$50,000" may have an equal (or close to equal) proximity between the message sent at 12:02 PM and the message sent at 12:04 PM, because it is almost equally plausible that the user was responding to either message (based on the times each message was sent). However, in another example, if the message "$50,000" was not sent until 5:00 PM that afternoon, then it is more likely that the user actually read both messages and was responding to the most recent message, therefore the "$50,000" message may have a closer proximity to the "How much is remaining on your mortgage for your house?" message than the "What is your yearly salary?" message. In some embodiments, proximity is indicated using an integer, decimal, percent, category, etc. In some instances, proximity measuring techniques such as Hadamard Distance or Latent Dirichlet Model, may be used to determine the proximity between conversation elements.

Determining whether any conversation elements include linked concepts includes operation 232 to determine whether the proximity between the conversation elements is below a threshold proximity. In some embodiments, the threshold proximity is a predetermined proximity (indicated by a value, decimal, percent, category, etc.) determined by the provider system or the AI system. In some embodiments, the proximity threshold is determined through analyzing historical AI conversational platforms and determining a proximity where associated conversation elements are no longer, or at least much less frequently, being misinterpreted. In some instances, a small proximity (for example, a small proximity value) indicates that the associated conversation elements are in close proximity to each other. For example, a proximity of zero may indicate that associated conversation elements are right next to each other. In these instances, a proximity below a threshold indicates that the proximity of the associated elements are closer than the threshold proximity. In some instances, if a high proximity indicates that the associated conversation elements are in close proximity to each other, then operation 232 becomes determining whether a proximity is above a threshold proximity, as associated conversation elements that are in close proximity to each other may be more likely to be misunderstood or misinterpreted by the AI assistant.

If the proximity between the conversation elements is below a threshold proximity, then it is determined, in operation 234, that there are linked conversation elements, as the conversation elements include linked concepts and are in close proximity to each other. If the proximity between the conversation elements is not below the threshold proximity, then it is determined, in operation 236, that there are not any linked conversation elements, as the conversation elements are far enough apart (in proximity) that any linked concepts between the two conversation elements may be coincidental, not related to the same specific issue, etc. For example, the same communication could discuss where a user's head hurts and also a treatment suggestion to put ice on a bruised forehead. In this example, the two conversation elements may be associated conversation elements, because they are both discussing head pain for a user, however there may be enough distance between the two conversation elements, that the system (correctly) determined that the elements were not actually discussing the same issue, as one element was discussing diagnosing and the other element was discussing treating the injury.

In some embodiments, operations 222 through 236 may be repeated for each conversation element within the communication.

Method 200 proceeds to operation 240 to determine whether the linked conversation elements include critical data. Critical data, as discussed herein, may be data within the conversation elements that is critical, or very important, in performing the various actions (for example, diagnosing, treating, etc. for healthcare situations). Determining whether the linked conversation elements include critical data may include analyzing each component of each linked conversation element and determining a purpose and/or characterizing each component. For example, "my foot hurts" includes three components, one indicating who's foot hurts, the second indicating what hurts, and the third indicating what the injury/ailment is. The purposes of all three components may be categorized as diagnosing the issue, therefore the example conversation element includes critical data. In another example, "I don't need more help" does not include any components related to diagnosing or treating an issue, therefore this conversation element may not include any critical data.

Figure 3:
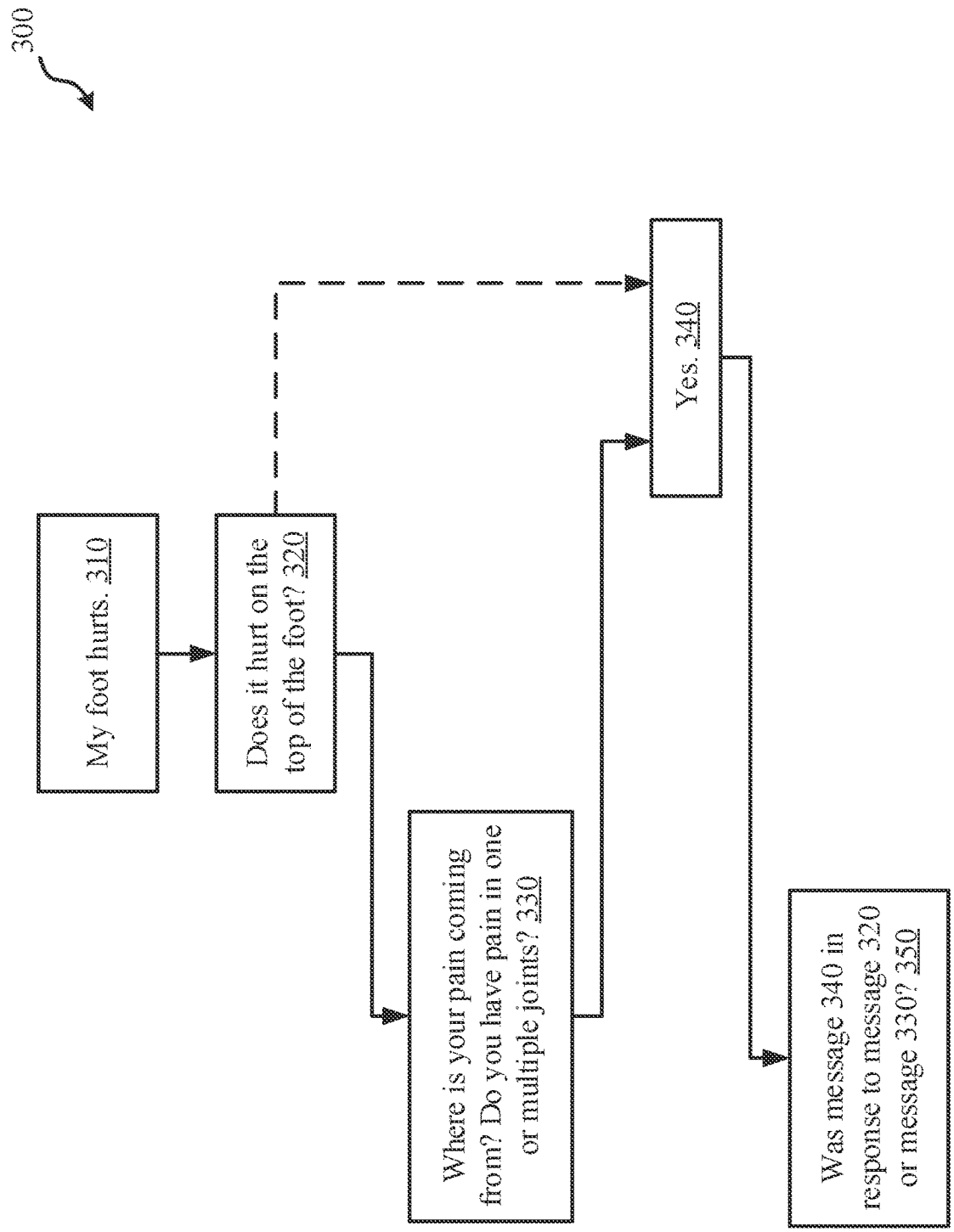
FIG. 3 depicts a block diagram of an example conversation tree, according to some embodiments.

Referring to FIG. 3, a block diagram of an example conversation tree 300 is depicted, according to some embodiments. Conversation tree 300 outlines conversation elements between a user (for example, communicating through user system 410 (FIG. 4)) and an AI assistant (for example, AI system 422 (FIG. 4)). In example conversation tree 300, a user system transmitted message 310 to an AI system, the message stating, "My foot hurts." The AI system responded with message 320 "Does it hurt on the top of the foot?" Then, the AI system sent a second message 330 (for example, after receiving no response from the user) asking "Where is your pain coming from? Do you have pain in one or multiple joints?" Then, after message 330, the user system replied with message 340 "Yes." However, in conversation tree 300, it is unclear whether message 340 is in response to message 330 or message 320, as the message could reasonably apply to either inquiry. In this example, if it is determined, as depicted, that message 340 was in response to message 330, then the user may start being treated for joint pain (perhaps arthritis) and the AI system may start suggesting arthritis treatments. However, if the user intended for message 340 to be in response to message 320, then the user may not have arthritis and/or joint pain at all, and may instead, for example, have a bruised foot. In some instances, being treated for the incorrect ailment may injure or harm the user, or at the very least, may not accurately treat the user for their actual ailment.

In conversation tree 300, the system may have already determined that messages 320, 330, and 340 contain a critical sequence of data (for example, using method 100 (FIG. 1) and, in some instances, 200 (FIG. 2)). Once it is determined that the messages 320, 330, and 340 contain a critical sequence of data, the system may determine how uncertain it is that the AI system will correctly interpret the critical sequence of data (for example, by correctly interpreting whether message 340 was responding to message 320 or 330). In some instances, uncertainty is indicated using an uncertainty level.

Predicting an uncertainty level for interpreting message 340 (and the critical sequence of data of messages 320, 330, and 340) may include analyzing conversation elements surrounding the critical sequence data (and the critical sequence data itself) and determining whether there are multiple interpretations of the critical sequence data. In some embodiments, message 350 may not have been sent yet in conversation tree 300. Therefore, the conversation elements surrounding the critical sequence data include message 310 and the critical sequence data itself of messages 320, 330, and 340. In some instances, the conversation elements may be analyzed in parallel, in inverse, and in forward form. Therefore, in these instances, analyzing the elements in parallel includes analyzing messages 310, 320, 330, and 340 as if they were sent at the same time. When analyzing the messages in parallel, it may be determined that message 340 is in response to message 320, as message 340 answers all inquiries from message 320 (where message 330 would still have open inquiries even if message 340 was responding to message 330). When analyzing in forward form, conversation tree 300 may be analyzed as if the messages were intended to be interpreted in the order they were sent, or message 310 to message 320, message 320 to message 330, and message 330 to message 340. In forward form, message 340 may be interpreted as replying to message 330, as the message is subsequent message 330. Similarly, when analyzing in reverse form (message 340 to 330, 330 to 320, and 320 to 310), message 340 may also be interpreted as replying to message 330, as the messages are closest in proximity to each other. Therefore, because message 340 is not always interpreted as replying to the same message (320 or 330), it may be determined that there is some uncertainty for interpreting message 340.

In some instances, predicting an uncertainty level may include determining a percent (or an integer, decimal, etc.) of interpretation for each analysis method (e.g., forward, reverse, and parallel). The percent of interpretation may include how likely the critical sequence data is to be interpreted each way for each analysis method. For example, when analyzing in parallel, message 340 may be 75% likely to be in reply to message 320 and 25% likely to be in reply to message 330. When analyzing in forward, message 340 may be 30% likely to be in reply to message 320 and 70% likely to be in reply to message 330. When analyzing in reverse, message 340 may be 40% likely to be in reply to message 320 and 60% likely to be in reply to message 330. In some instances, the uncertainty level may be based on the percent of interpretation. Here, because the percent varies based on the analysis method, the critical sequence data may be determined to be highly uncertain.

Predicting an uncertainty level for interpreting message 340 (and the critical sequence of data of messages 320, 330, and 340) may also include determining consequences of the multiple interpretations. To determine the consequences, it may be predicted how likely the multiple interpretations of the critical sequence data are to any change actions (for example, treatments, diagnoses, etc.) in response to the critical sequence data. As discussed above, interpreting message 340 as responding to 330 or interpreting message 340 as responding to message 320 may have a significant effect on what treatment suggestions the AI assistant sends to the user. The AI assistant may treat the user for arthritis or joint pain of message 340 is in response to message 330 and may treat the user, for example, for a bruised foot if message 340 is in response to message 320. Therefore, in conversation tree 300, it is very likely that the multiple interpretations of the critical sequence data are to any change actions (such as treating the user). In another example, not depicted, message 330 may have included a rephrasing of message 320 such as "Is the top of your foot where your pain is?" In this instance, interpreting message 340 as a response to message 330 or 320 may not have made much of a difference, because either way message 340 would have been clarifying that the top of the foot is what hurts. Therefore, in that example, there may not have been much uncertainty for the critical sequence data.

Then, based on the uncertainty level, it may be determined whether the critical sequence data is subject to misinterpretation (for example, in operation 150 (FIG. 1)). If the critical sequence data has a high uncertainty level, then the critical sequence data is subject to misinterpretation. If the critical sequence data has a low uncertainty level, then the critical sequence data may not be subject to misinterpretation. In some instances, if there is any uncertainty in interpreting the critical sequence data, then the critical sequence data may be subject to misinterpretation. In conversation tree 300, the critical sequence data of messages 320, 330, and 340 have a high uncertainty level, therefore it is determined that the critical sequence data is subject to misinterpretation.

In conversation tree 300, after determining that the critical sequence data (including messages 320, 330, and 340) were subject to misinterpretation, the AI assistant transmitted message 350, to clarify whether message 340 was in response to message 330 or message 320. Once the user clarifies what they intended with message 340, the AI assistant may proceed with the necessary questioning in order to properly diagnose and treat the user.

Figure 4:
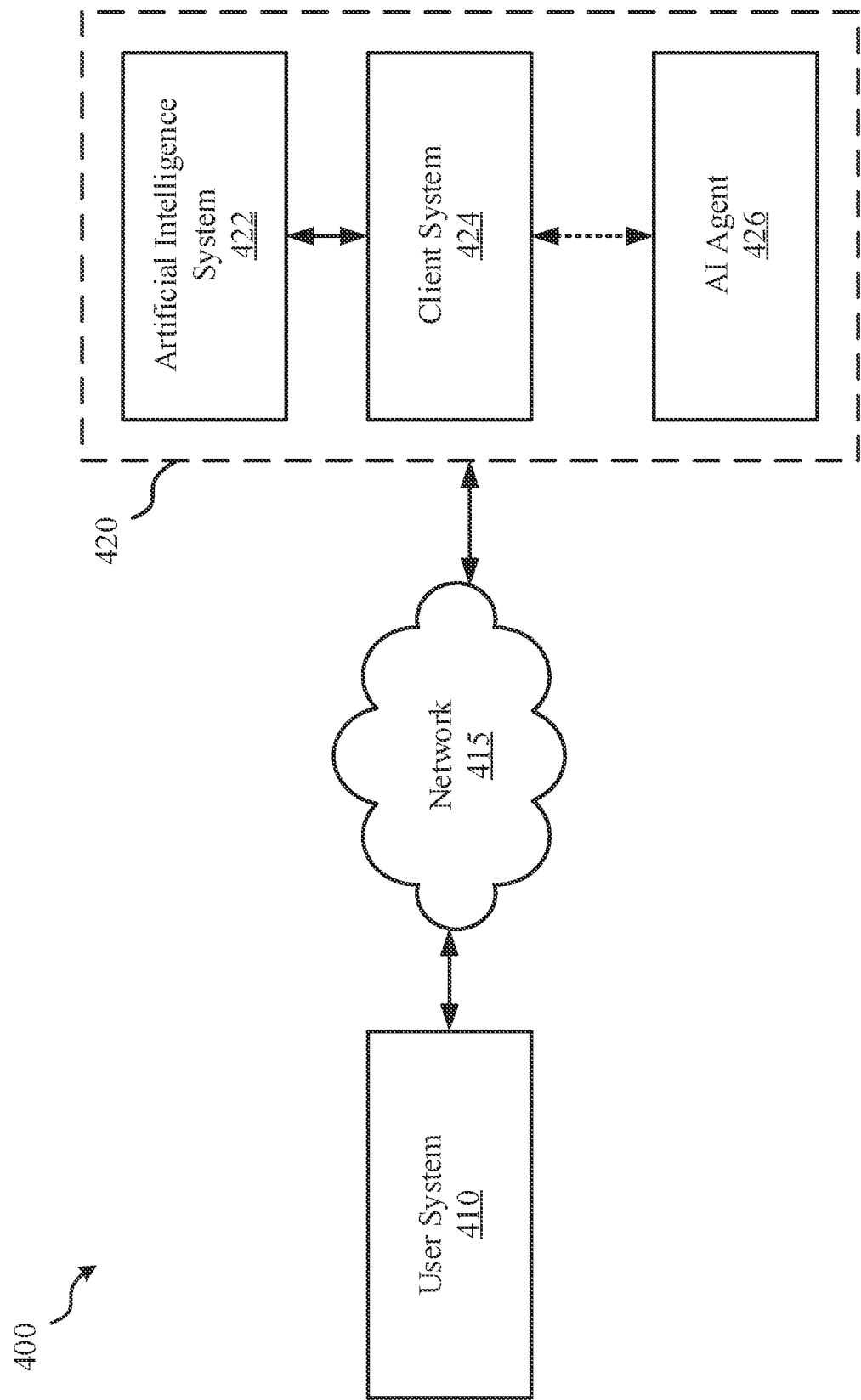
FIG. 4 depicts a block diagram of an example AI conversation environment, according to some embodiments.

Referring to FIG. 4, a block diagram of an example artificial intelligence (AI) conversation environment 400 is depicted, according to some embodiments. AI conversation environment 400 includes a user system 410 and a provider system 420, connected via a network 415. In some instances, the user system 410 is searching for information (such as receiving healthcare treatment suggestions, finance suggestions, etc.) and the provider system 420 is providing the information. In some embodiments, provider system 420 performs method 100 (FIG. 1) and method 200 (FIG. 2). Provider system 420 includes an artificial intelligence system 422 and a client system 424. FIG. 4 depicts AI system 422 and client system 424 as separate (but connected) systems, however client system 424 and AI system 422 may be the same system, in some embodiments. Provider system 420 also includes AI agent 426. In some embodiments, AI agent 426 is the AI assistant that converses (e.g., via a communication) with the user through the user system 410. AI system 422 provides the AI technology and processing to the AI agent 426. In some embodiments (not depicted), AI agent 426 is a part of AI system 422. In some embodiments, AI agent 426 is connected to AI system 422. AI agent 426 is also connected to client system 424. In some instances, client system 424 may be a client, such as a healthcare client, that provides all the data (such as the healthcare data and treatment suggestions) to the user system 410 and the user (not depicted). In some embodiments, the AI system 422, the client system 424, and the AI agent 426 are all part of the same system. In some embodiments, the AI system 422, the client system 424, and the AI agent 426 are separate, but connected, systems.

Figure 5:
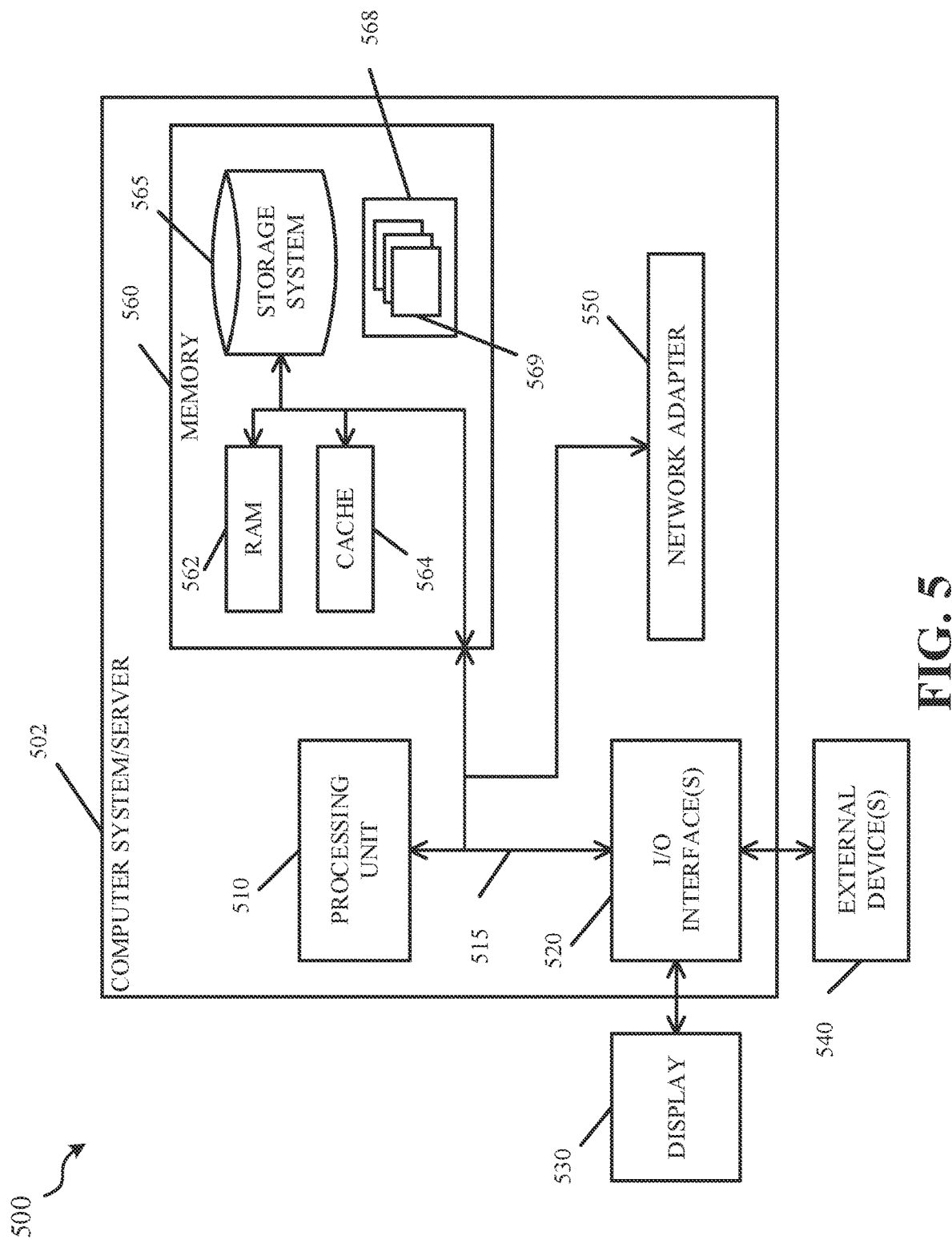
FIG. 5 depicts a block diagram of an example computer system environment, according to some embodiments.

Referring to FIG. 5, computer system 500 is a computer system/server 502 is shown in the form of a general-purpose computing device, according to some embodiments. In some embodiments, computer system/server 502 is located on the linking device. In some embodiments, computer system 502 is connected to the linking device. The components of computer system/server 502 may include, but are not limited to, one or more processors or processing units 510, a system memory 560, and a bus 515 that couples various system components including system memory 560 to processor 510.

Bus 515 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 502 typically includes a variety of computer system readable media. Such media may be any available media that is accessible by computer system/server 502, and it includes both volatile and non-volatile media, removable and non-removable media.

System memory 560 can include computer system readable media in the form of volatile memory, such as random-access memory (RAM) 562 and/or cache memory 564. Computer system/server 502 may further include other removable/non-removable, volatile/non-volatile computer system storage media. By way of example only, storage system 565 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 515 by one or more data media interfaces. As will be further depicted and described below, memory 560 may include at least one program product having a set (e.g., at least one) of program modules that are configured to carry out the functions of embodiments of the disclosure.

Program/utility 568, having a set (at least one) of program modules 569, may be stored in memory 560 by way of example, and not limitation, as well as an operating system, one or more application programs, other program modules, and program data. Each of the operating system, one or more application programs, other program modules, and program data or some combination thereof, may include an implementation of a networking environment. Program modules 569 generally carry out the functions and/or methodologies of embodiments of the invention as described herein.

Computer system/server 502 may also communicate with one or more external devices 540 such as a keyboard, a pointing device, a display 530, etc.; one or more devices that enable a user to interact with computer system/server 502; and/or any devices (e.g., network card, modem, etc.) that enable computer system/server 502 to communicate with one or more other computing devices. Such communication can occur via Input/Output (I/O) interfaces 520. Still yet, computer system/server 502 can communicate with one or more networks such as a local area network (LAN), a general wide area network (WAN), and/or a public network (e.g., the Internet) via network adapter 550. As depicted, network adapter 550 communicates with the other components of computer system/server 502 via bus 515. It should be understood that although not shown, other hardware and/or software components could be used in conjunction with computer system/server 502. Examples include, but are not limited to: microcode, device drivers, redundant processing units, external disk drive arrays, RAID systems, tape drives, and data archival storage systems, etc.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electronic signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object orientated program language such as Smalltalk, C++, or the like, and procedural programming languages, such as the "C" programming language or similar programming languages. The computer readable program instructions may execute entirely one the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to some embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method comprising:
monitoring an artificial intelligence enabled communication between an artificial intelligence assistant and a user;
analyzing messages, participants, and actions within the communication;
identifying critical data within the communication, wherein the critical data is data within conversation elements of the communication that is important for performing the actions within the communication;
determining critical sequence data, wherein the critical sequence data is a sequence of the conversation elements that is within the communication and that contains the critical data;
predicting an uncertainty level for the critical sequence data, wherein the uncertainty level indicates an amount of uncertainty that the artificial intelligence assistant correctly interprets the critical sequence data;
determining that the uncertainty level for the critical sequence data is above a threshold uncertainty value, resulting in critical sequence data that is subject to misinterpretation from the artificial intelligence assistant; and
in response to determining that the critical sequence data is subject to misinterpretation, resolving any uncertainties for the critical sequence data prior to concluding a communication sequence, within the communication, related to the critical data.

2. The method of claim 1, wherein determining critical sequence data comprises:
analyzing linked concepts and unlinked concepts within the communication;
determining, based on the analyzing, whether any conversation elements comprise linked concepts, resulting in linked conversation elements; and
determining whether the linked conversation elements comprise the critical data.

3. The method of claim 2, wherein determining whether any conversation elements comprise linked concepts comprises:
analyzing each conversation element of the communication;
determining whether the concepts within each conversation element are associated with other conversation elements within the communication;

in response to determining that the concepts within a first conversation element from the conversation elements are associated with an other conversation element within the communication, determining a proximity between the first conversation element and the other conversation element;

determining whether the proximity between the first conversation element and the other conversation element is below a threshold proximity; and in response to determining that the proximity between the first conversation element and the other conversation element is below the threshold proximity, determining that the first conversation element and the other conversation element are linked.

4. The method of claim 3, further comprising:

in response to determining that the concepts within a second conversation element are not associated with the other conversation elements within the conversation, determining whether concepts within the second conversation element are unresolved and will be resolved in a future conversation element; and in response to determining that the concepts within the second conversation element are unresolved and will be resolved in the future conversation element, determining that the concepts within the conversation element are associated with the future conversation element.

5. The method of claim 1, wherein predicting the uncertainty level for the critical sequence data comprises:

analyzing conversation elements surrounding the critical sequence data; and determining whether there are multiple interpretations of the critical sequence data based on the conversation elements surrounding the critical sequence data.

6. The method of claim 5, wherein predicting the uncertainty level for the critical sequence data further comprises determining consequences of the multiple interpretations of the critical sequence data, wherein determining the consequences comprises:

predicting how likely the multiple interpretations of the critical sequence data are to change actions in response to the critical sequence data.

7. The method of claim 5, wherein analyzing the conversation elements surrounding the critical sequence data comprises:

analyzing the conversation elements in parallel form, in inverse form, and in forward form.

8. The method of claim 1, wherein resolving any uncertainties for the critical sequence data comprises:

determining that a conversation element related to the critical sequence data has not been received; and stopping progress in any conversation elements relating to the critical sequence data until the one or more conversation elements are received.

9. The method of claim 1, wherein resolving any uncertainties for the critical sequence data comprises:

identifying any conversation elements with the critical sequence data, resulting in critical conversation elements; and labelling the critical conversation elements as unresolved.

10. The method of claim 1, wherein resolving any uncertainties for the critical sequence data comprises:

transmitting one or more clarifying inquiries to a user, the one or more clarifying inquiries querying the user to clarify one or more conversation elements relating to the critical sequence data.

11. The method of claim 1, wherein the artificial intelligence enabled communication is a healthcare communication.

12. A system having one or more computer processors, the system configured to:

monitor an artificial intelligence enabled communication between an artificial intelligence assistant and a user;

analyze messages, participants, and actions within the communication;

identify critical data within the communication, wherein the critical data is data within conversation elements of the communication that is important for performing the actions within the communication;

determine critical sequence data, wherein the critical sequence data is a sequence of the conversation elements that is within the communication and that contains the critical data;

predict an uncertainty level for the critical sequence data, wherein the uncertainty level indicates an amount of uncertainty that the artificial intelligence assistant correctly interprets the critical sequence data;

determine that the uncertainty level for the critical sequence data is above a threshold uncertainty value, resulting in critical sequence data that is subject to misinterpretation from the artificial intelligence assistant; and in response to determining that the critical sequence data is subject to misinterpretation, resolve any uncertainties for the critical sequence data prior to concluding a communication sequence, within the communication, related to the critical data.

13. The system of claim 12, wherein determining critical sequence data comprises:

analyzing linked concepts and unlinked concepts within the communication;

determining, based on the analyzing, whether any conversation elements comprise linked concepts, resulting in linked conversation elements; and determining whether the linked conversation elements comprise the critical data.

14. The system of claim 13, wherein determining whether any conversation elements comprise linked concepts comprises:

analyzing each conversation element of the communication;

determining whether the concepts within each conversation element are associated with other conversation elements within the communication;

in response to determining that the concepts within a first conversation element from the conversation elements are associated with an other conversation element within the communication, determining a proximity between the first conversation element and the other conversation element;

determining whether the proximity between the first conversation element and the other conversation element is below a threshold proximity; and in response to determining that the proximity between the first conversation element and the other conversation element is below the threshold proximity, determining that the first conversation element and the other conversation element are linked.

15. The system of claim 12, wherein predicting the uncertainty level for the critical sequence data comprises:

analyzing conversation elements surrounding the critical sequence data; and determining whether there are multiple interpretations of the critical sequence data based on the conversation elements surrounding the critical sequence data.

16. The system of claim 12, wherein resolving any uncertainties for the critical sequence data comprises:
   identifying any conversation elements with the critical sequence data, resulting in critical conversation elements; and
   labelling the critical conversation elements as unresolved.

17. A computer program product comprising a computer readable storage medium having program instructions embodied therewith, the program instructions executable by a server to cause the server to perform a method, the method comprising:
   monitoring an artificial intelligence enabled communication between an artificial intelligence assistant and a user;
   analyzing messages, participants, and actions within the communication;
   identifying critical data within the communication, wherein the critical data is data within conversation elements of the communication that is important for performing the actions within the communication;
   determining critical sequence data, wherein the critical sequence data is a sequence of the conversation elements that is within the communication and that contains the critical data;
   predicting an uncertainty level for the critical sequence data, wherein the uncertainty level indicates an amount of uncertainty that the artificial intelligence assistant correctly interprets the critical sequence data;
   determining that the uncertainty level for the critical sequence data is above a threshold uncertainty value, resulting in critical sequence data that is subject to misinterpretation from the artificial intelligence assistant; and
   in response to determining that the critical sequence data is subject to misinterpretation, resolving any uncertainties for the critical sequence data prior to concluding a communication sequence, within the communication, related to the critical data.

18. The computer program product of claim 17, wherein determining critical sequence data comprises:
   analyzing linked concepts and unlinked concepts within the communication;
   determining, based on the analyzing, whether any conversation elements comprise linked concepts, resulting in linked conversation elements; and
   determining whether the linked conversation elements comprise the critical data.

19. The computer program product of claim 18, wherein determining whether any conversation elements comprise linked concepts comprises:
   analyzing each conversation element of the communication;
   determining whether the concepts within each conversation element are associated with other conversation elements within the communication;
   in response to determining that the concepts within a first conversation element from the conversation elements are associated with an other conversation element within the communication, determining a proximity between the first conversation element and the other conversation element;
   determining whether the proximity between the first conversation element and the other conversation element is below a threshold proximity; and
   in response to determining that the proximity between the first conversation element and the other conversation element is below the threshold proximity, determining that the first conversation element and the other conversation element are linked.

20. The computer program product of claim 17, wherein predicting the uncertainty level for the critical sequence data comprises:
   analyzing conversation elements surrounding the critical sequence data; and
   determining whether there are multiple interpretations of the critical sequence data based on the conversation elements surrounding the critical sequence data.

* * * * *